United States Patent [19]

Favonio

[11] 4,310,309
[45] Jan. 12, 1982

[54] DENTAL BUR DRILL
[75] Inventor: Osvaldo Favonio, Ornago, Italy
[73] Assignee: FARO Fabbrica Apparecchiature Razionali Odontoiatriche S.p.A., Ornago, Italy
[21] Appl. No.: 147,307
[22] Filed: May 6, 1980
[30] Foreign Application Priority Data
   May 9, 1979 [IT] Italy ................................ 22506 A/79
[51] Int. Cl.³ ........................................ A61C 1/08
[52] U.S. Cl. ........................................ 433/104; 415/112
[58] Field of Search ................... 433/104, 82; 415/112
[56] References Cited
   U.S. PATENT DOCUMENTS

| | | | |
|---|---|---|---|
| 2,977,682 | 4/1961 | Flatray | 433/104 |
| 2,988,815 | 6/1961 | Staunt | 433/104 |
| 3,069,775 | 12/1962 | Hawtin | 433/104 |
| 3,189,999 | 6/1965 | Reiter | 433/104 |
| 3,197,869 | 8/1965 | Staunt | 433/104 |
| 3,879,851 | 4/1975 | Landgraf | 433/104 |
| 4,218,216 | 8/1980 | Sugai et al. | 433/104 |

Primary Examiner—Gene Mancene
Assistant Examiner—John J. Wilson
Attorney, Agent, or Firm—Oblon, Fisher, Spivak, McClelland & Maier

[57] ABSTRACT

A dental bur drill of the type including a tubular handpiece traversed by at least one conduit for delivering compressed air to a rotor which is mounted at an extreme end portion of said handpiece and to the bearing-mounted rotating shaft to which a bur is fitted, wherein the handpiece incorporates a lube-oil container provided with an injection nozzle protruding within a delivery conduit, which conduit communicates with the container at a point upstream of the nozzle.

4 Claims, 1 Drawing Figure

U.S. Patent   Jan. 12, 1982   4,310,309
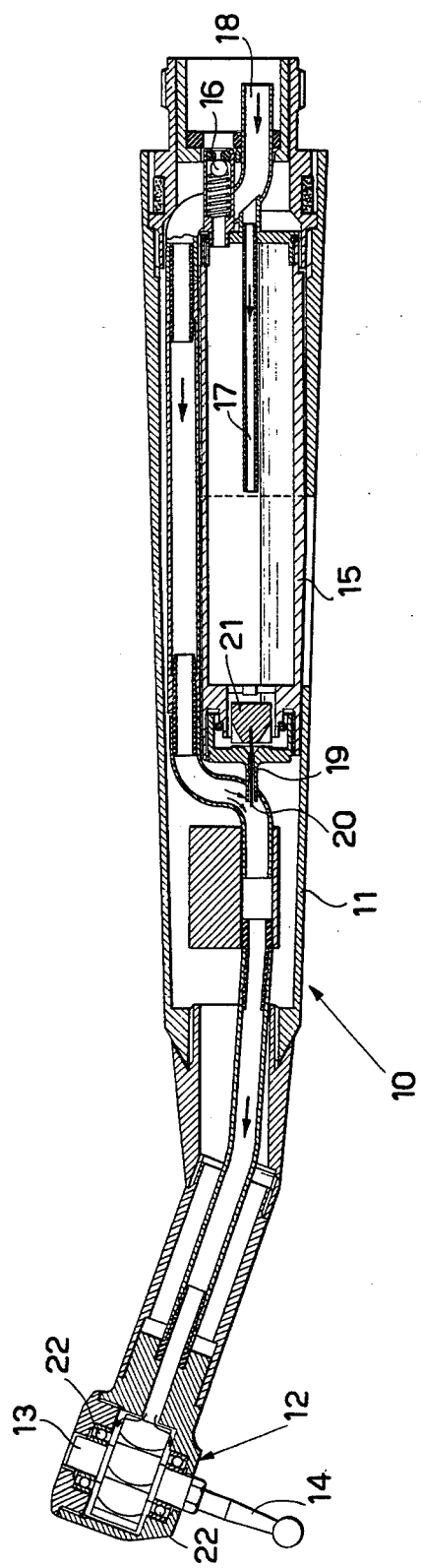

DENTAL BUR DRILL

BACKGROUND OF THE INVENTION

1. Field of the Invention

The present invention relates to a drill and more particularly to a dental bur drill.

2. Description of the Prior Art

As is well known to persons skilled in the art, one of the major problems to be solved in designing a dental bur drill concerns the lubrication of the rotor shaft to which the bur is connected. In the bur drills currently used, the rotor shaft in fact rotates at a speed ranging from 200,000 to 600,000 rpm. It is therefore essential to provide the bearings with adequate lubrication, since otherwise they overheat and become unserviceable.

One method of lubrication already known provides for the spraying of nebulized oil into the interior of the bearing cage by means of a spray-cylinder, through the air supply conduit. This system requires that the dental surgeon lubricate the bearings at the start of every working day since if this is overlooked the bearings become unserviceable because each injection of lube-oil provides an autonomy of only one working day approximately.

Another known system includes a nebulizer installed upstream of the rotor which automatically sends the lubricant to the rotor bearings by means of a calibrated solenoid valve. A lubrication method of this kind has the disadvantage of being relatively costly and bulky, requiring as it does an installation separate from the bur drill.

SUMMARY OF THE INVENTION

The purpose of the present invention is to obviate the aforesaid inconveniences of the known art, and to achieve such purpose the invention proposes a dental bur drill of the type including a tubular handpiece run through by at least one compressed air conduit delivering the air to a rotor which is mounted at the extremity (i.e. on extreme end portion) of the handpiece and to the bearing-mounted rotating shaft of which a bur is fitted, wherein the handpiece incorporates a lubricant container provided with an injection nozzle protruding into the interior of the delivery conduit, which conduit also communicates with the container at a point upstream of the nozzle.

In this manner, nebulized lubricant is entrained by the compressed air, which can be used either for the operation of the rotor or only for the internal lubrication of the bearing cage, the bearings thus being assured an adequate lubrication of an automatic and continuous kind.

BRIEF DESCRIPTION OF DRAWINGS

The structural and functional characteristics of the invention and its advantages will be better understood from the following exemplifying description, referred to the attached drawing wherein: The sole FIGURE illustrates, in longitudinal section, a dental bur drill embodying the principles of the invention.

DESCRIPTION OF THE PREFERRED EMBODIMENT

With reference to the drawing, the bur drill according to the invention is indicated overall by reference number 10, and includes a tubular handpiece 11 which terminates in a rotor 12 to the shaft 13 of which a bur 14 is fitted.

According to the present invention, the handpiece 11 incorporates a lube-oil container 15, which is fillable through a ball valve 16. Upstream, the container 15 communicates through an axial tube 17 with a conduit 18 for delivery of compressed air to the rotor 12 and, downstream, communicates with the said conduit 18 through a nozzle 19 for injection of the lube-oil of the container 15. The nozzle 19 extends for a certain length inside the conduit 18 and is run through by a needle 20, or similar device, which can also be provided at one end with a weight 21. In this manner, when the bur drill is inclined, the needle 20 is constrained to run along the nozzle 19, so as to keep it permanently clean.

The operation of the bur drill described above is, briefly, as follows an equal pressure is set up inside the container 15 and the conduit 18. However, the nozzle 19 which protrudes into the conduit 18 causes a sectional narrowing therein and, as a result of this, the air undergoes an acceleration which causes a certain vacuum at the immediate outlet of the said nozzle 19. Thus, the lube-oil in the container 15 is entrained in the stream of air into the interior of the conduit 18 and is there dispersed into small particles (nebulized) and carried for lubrication purposes to the bearings 22 of the rotor shaft.

When the rotor is operating, its bearings are in this manner assured automatic and continuous lubrication. All that the dental surgeon is required to do is to top-up the oil level in the container 15 when it falls to below a pre-established limit which can be verified from the outside of the hand-piece, for example through a small window-slot.

With the handpiece in a horizontal position, the maximum level of the oil remains lower than the tube 17 communicating with the conduit 18, with the result that if the handpiece is inclined the oil cannot enter the air conduit 18 upstream of the nozzle 19.

Communication between the tube 17 and the conduit 18 has the purpose of bringing the pressure inside the container back to atmospheric pressure when work is discontinued. The resulting bur drill is consequently a bur drill provided with a method for the automatic lubrication of the rotor bearings which obviates the inconveniences of the known art, mentioned in the introduction.

Only one possible form of embodiment of the invention has been illustrated and described; variants and modifications can, however, be made to it without falling outside the scope of the invention as defined in the following claims.

What is claimed as new and desired to be secured by Letters Patent of the United States is:

1. A dental bur drill comprising:
   a tubular handpiece traversed by at least one conduit;
   a rotor having a bearing-mounted shaft mounted at an extreme and portion of said handpiece wherein said conduit delivers compressed air to said rotor and to said bearing-mounted rotating shaft;
   a bur fitted to said bearing-mounted shaft;
   a lube-oil container mounted in said handpiece;
   an injection nozzle protruding from said container and extending within said conduit wherein said conduit communicates with said container at a point upstream of said nozzle; and
   a needle which traverses said injection nozzle.

2. A bur drill according to claim 1, said container further comprising a filler valve.

3. A bur drill according to claim 1, further comprising a tube which extends axially within said container and that an extreme end portion thereof is opposite said injection nozzle.

4. A bur drill according to claim 1, further comprising a weight attached to said needle.

* * * * *